United States Patent [19]

Wurtman

[11] Patent Number: 4,542,123

[45] Date of Patent: Sep. 17, 1985

[54] COMPOSITION AND METHOD FOR INCREASING BRAIN TYROSINE LEVELS

[75] Inventor: Richard J. Wurtman, Boston, Mass.

[73] Assignee: Massachusetts Institute of Technology, Cambridge, Mass.

[21] Appl. No.: 338,682

[22] Filed: Jan. 11, 1982

[51] Int. Cl.[4] ........................ A61K 37/26; A61K 31/70
[52] U.S. Cl. ........................................ 514/3; 514/23; 514/53; 514/4
[58] Field of Search ................................ 424/180, 178

[56] References Cited

U.S. PATENT DOCUMENTS

| | | | |
|---|---|---|---|
| 4,095,000 | 6/1978 | Brenner | 424/180 |
| 4,182,756 | 1/1980 | Ramsay et al. | 424/180 |
| 4,210,637 | 7/1980 | Wurtman et al. | 424/180 |
| 4,221,906 | 9/1980 | Querry et al. | 424/180 |
| 4,289,688 | 9/1981 | Hotta et al. | 424/180 |

*Primary Examiner*—Johnnie R. Brown
*Attorney, Agent, or Firm*—Arthur A. Smith, Jr.; Paul J. Cook

[57] ABSTRACT

A composition comprising tyrosine and a carbohydrate is administered in amount to increase brain tyrosine levels.

12 Claims, No Drawings

COMPOSITION AND METHOD FOR INCREASING BRAIN TYROSINE LEVELS

BACKGROUND OF THE INVENTION

The Government has rights in this invention pursuant to Grant No. AM 14228 awarded by the National Institute of Health.

This invention relates to a method and composition for increasing brain levels of tyrosine.

Prior to the present invention, it has been shown that increased brain levels of tyrosine in normal humans can result in improved mood, vigor and alertness. In addition, it has been shown that increased tyrosine blood levels results in increased dopamine, norepinephrine or epinephrine release in brain synapses which is useful in treating neurologic diseases including depression, hypertension, cardiac arrhythmias, Parkinson's Disease, hyperprolactinemia and shock.

It has been shown in U.S. Pat. No. 4,210,637 that carbohydrate administered in conjunction with tryptophan increases the normal effect of tryptophan for increasing brain serotonin levels. The administered carbohydrate results in insulin secretion in the patient. Tryptophan has an anomalous response to insulin in that its plasma levels do not fall when insulin plasma levels are increased. In contrast, tyrosine plasma levels as well as plasma levels of other large neutral amino acids (LNAA) fall when plasma insulin levels increase.

It would be desirable to provide a means for controlling blood plasma levels of tyrosine and other amino acids in a manner to effect an increase in brain tyrosine level. Furthermore, it would be desirable to provide such a means which minimizes the amount of tyrosine administered to a patient.

SUMMARY OF THE INVENTION

The present invention provides a method and composition for increasing brain levels of tyrosine. This invention is based upon the discovery that a combination of tyrosine and a carbohydrate (which causes insulin secretion) selectively reduces plasma levels of large neutral amino acid (LNAA) to a greater extent than tyrosine is reduced so that there is reduced competition for tyrosine intake in the brain. The mixture of tyrosine and an insulin-secreting carbohydrate can be administered alone or with a methylxanthine caffeine or another mild stimulant, to override the sedating effects of the carbohydrate.

DESCRIPTION OF THE SPECIFIC EMBODIMENTS

In accordance with this invention, tyrosine and an insulin-releasing carbohydrate are administered to a patient. The administration of a carbohydrate that releases insulin decreases the plasma levels of the other neutral amino acids normally found in the plasma such as leucine, isoleucine, phenylalamine and valine. Thus, the carbohydrate causes an increase of the plasma levels of tyrosine in relation to these other amino acids by decreasing the concentration of the other amino acids in the plasma to a greater extent than the reduction of tyrosine.

Representative suitable carbohydrates for this invention include sucrose, dextrose, starch, fructose, invert sugar, dextrins, sugar polymers such as polyose, xylitol and mixtures thereof or the like. The amount of carbohydrate administered should be such as to lower plasma LNAA levels between about 10 and 40%. Said amount is physiologically equivalent to between about 5 and 50 grams of glucose. The relative proportion of tyrosine to the insulin-releasing carbohydrate can vary widely so long as there is a cumulative effect on neuronal dopamine or norepinephrine synthesis by the two components utilized in the composition of this invention. Generally, the weight ratio of the tyrosine to the carbohydrate(s) is between about 1:5 and about 1:100 more usually between about 1:20 and 1:50. The compositions of this invention are administered in an amount sufficient to effect increase in brain tyrosine levels while not being administered in such large amounts as to seriously reduce the brain levels of other neurotransmitters needed for normal functioning such as serotonin, acetylcholine or the non-essential amino acids. Typical unit dosage form useful for oral administration ranges between about 0.25 grams and about 10.0 grams (i.e. of tyrosine) and more usually between about 0.5 and 2.0 grams.

The mixture can be administered as free tyrosine, tyrosine esters or salts, natural or synthetic polymers, or as constituents of food. The route of administration will generally be oral, for example, as a tablet, sustained-release capsule, drink, beverage sweetener, wafer, candy, chewing gum or enteral mixture. It may be mixed with a mild stimulant like caffeine for daytime use (to override the sedative effect of carbohydrate) or used without a mild stimulant at nighttime. The mixture may also be presented as a parenteral solution, e.g. in treatment of shock.

The following examples illustrate the present invention and are not intended to limit the same.

EXAMPLE I

This example illustrates that administration of an insulin-releasing carbohydrate results in a greater decrease in LNAA plasma levels as compared to decrease in tyrosine plasma levels.

Six healthy, non-obese, fasting subjects each received, on different days 0, 6, 12.5, 25 or 50 g of glucose (Glucola) in a total volume of 100 ml. Blood was taken at intervals and assayed for plasma levels of the branched-chain amino acids (valine, isoleucine and leucine); the other major large neutral amino acids (LNAA) (methionine, phenylalanine, tyrosine and tryptophan); and, in some cases, insulin and glucose. Insulin levels were significantly elevated 30 min after consumption of 12.5, 25 or 50 g of glucose concentrations were small and did not correlate with glucose dose. Mean percent reductions of LNAA tended to exhibit dose-dependence, most clearly observed after 120 min. In some subjects as little as 6 g of glucose transiently decreased LNAA concentrations. Branched-chain amino acids were most sensitive, decreasing by 35–41% after 50 g of glucose. Plasma tyrosine concentrations fell only by 23%, hence the ratio of plasma tyrosine to other plasma LNAA (which affects brain catecholamine synthesis) increased significantly.

Plasma concentrations of large, neutral amino acids (LNAA) in humans exhibit diurnal fluctuations that are generated by the cyclic ingestion of food and are dependent on meal composition: if the initial daily post-fasting meal (i.e., breakfast) is rich in carbohydrates and poor in proteins, it causes an insulin-mediated reduction in plasma LNAA other than tryptophan; however, if its protein content is greater than about 10% of total calories, its direct contribution of LNAA to the blood stream can overcome the insulin effect and cause LNAA levels to rise.

MATERIALS AND METHODS

Following a protocol approved by the Massachusetts Institute of Technology Committee on the Use of Humans as Experimental Subjects, 6 healthy volunteer outpatients, aged 25-33 years, participated in the study; 3 were males and 3 females. Mean weight was 60 kg for the women and 70 for the men; all subjects were within 10% of their ideal body weight as determined by Metropolitan Life Insurance Company tables. No subject was taking any medication and none had a family history of diabetes mellitus. Subjects were asked to take meals rich in carbohydrate content (about 300 g/day) for 3 days before beginning the study. On 5 separate days, each subject fasted from 8 p.m. until 9 the next morning and then received a load of 0, 6, 12.5, 25 or 50 g of glucose (caffeine-free glucola) dissolved in water in a total volume of 100 ml; the order of doses was randomized. Venous blood samples were drawn from the antecubital vein through an indwelling catheter at 0, 60 and 120 min for all doses and additionally at 30 and 180 min for the 12.5, 25 and 50 g doses. Blood was collected in heparanized tubes; after centrifugation plasma was stored at $-20°$ C. until analyzed. It was not possible to obtain blood for the last dose in subject 2 (0 g of glucose). Glucose was analyzed spectrophotometrically after reaction with O-toluidine in hot acidic acid (Sigma Bulletin #635;15). Insulin was measured using a commercial radioimmunoassay kit by a double antibody method (Bio-RIA, Louisville, Ky.). Plasma tryptophan was measured fluorometrically on 20 $\mu$l plasma aliquots by the method of Denckla and Dewey, J. Lab. Clin. Med. 69: 160-169, 1967, as modified by Lehman, Scand. J. Clin. Lab. Invest. 28: 49-55, 1971. Branched-chain amino acids and aromatic amino acids were measured in 500 $\mu$l aliquots of plasma, deproteinized with sulfosalicylic acid, using a Beckman amino acid analyzer (Beckman Instruments, Palo Alto, Calif., Model 119C).

Data, given as means $\pm$SE errors, were analyzed by two-way analysis of variance; factors compared were dose and time. The Scheffe test was employed to test the statistical significance of differences; $p<0.05$ was considered significant. Areas under the curves were evaluated by the method of trapezoid approximation. Student tests for paired data were used to evaluate the significance of changes in individual amino acids. Amino acid concentrations after treatments for each subject were also expressed as a percentage of that day's pretreatment levels; mean percent changes were then calculated for each treatment and time interval.

RESULTS

Following ingestion of 12.5, 25, or 50 g of glucose, mean plasma glucose concentrations rose after 30 min from 83$\pm$2.2 mg % to 105$\pm$8.6, 122$\pm$11.0, and 114$\pm$7.9 mg % respectively, and returned to baseline after 60-120 min Mean insulin concentrations increased from 9$\pm$0.9 $\mu$U/ml to 21.3$\pm$3.8, 44$\pm$5.0, and 58$\pm$6.9 $\mu$U/ml, respectively, after 30 min.

Glucose consumption caused a dose-related depression of plasma LNAA concentrations (expressed as percents of pre-treatment levels) after 60 and 120 min The decreases observed 60 and 120 min after subjects received the 25 and 50 g doses were significantly greater than those following the 0 and 6 g doses ($P<0.05$). Because of the high intra-individual and inter-individual variations in basal LNAA concentrations (especially for the branched-chain amino acids) there were no significant dose-related decreases in mean absolute LNAA concentrations. Glucose doses were highly correlated with the mean percent decreases in LNAA concentrations observed 120 min after treatments ($r=0.80$; $P<0.01$).

Among individual amino acids (Table 1) absolute isoleucine concentrations decreased significantly with time after all treatments (0-50 g glucose); leucine decreased significantly after 6-50 g; and all other amino acids decreased significantly after 12.5-50 g. Branched-chain amino acids concentrations decreased by 35-41% 120 min after subjects received 50 g of glucose; methionine by 31%, phenylalanine and tyrosine by 29-31%, and tryptophan by only 23% (Table 1). Because of this smaller reduction in plasma tryptophan, the tryptophan/LNAA ratio became elevated. In contrast, the tyrosine/LNAA ratio did not change significantly with any glucose dose.

Among 4 of the subjects (numbers 1, 3, 5 and 6), as little as 6 g of glucose may have been sufficient to reduce plasma LNAA at one or more of the times tested; subject 2 probably required 12.5 g, while subject 4 may have needed 25 g. Among subjects 2 and 4 there was a clear inverse linear relationship between the rise in plasma insulin after 12.5-50 g of glucose and the fall in LNAA (as assessed by calculating areas under the curve for each dose); this relationship was not robust for the other subjects. Even though the 50-g glucose does caused a greater elevation in insulin than the 25-g dose in 4 of the 6 subjects, it was not consistently associated with a greater percent reduction in plasma LNAA; the 50-g dose was associated with lower absolute concentrations of the amino acids than the 25-g dose after 120 min (Table I); however, for unknown reasons, zero-time plasma LNAA concentrations were also lower on days that subjects received 50 g than when they took the 25-g dose.

These data show that glucose consumption causes dose-related decreases in plasma LNAA concentrations among healthy young fasting subjects. In some subjects as little as 6 g of glucose is sufficient to decrease LNAA; larger doses (25-50 g) are needed to increase the plasma TRP/LNAA ratio, and thus to affect brain tryptophan and serotonin levels.

The observations indicate that even lower doses can elicit the secretion of sufficient insulin to the receptors that affect the flux of LNAA between the plasma and such tissues as skeletal muscle. The insulin-dependent uptake of the branched-chain amino acids into muscle, and their subsequent transamination or incorporation into protein, constitute the major mechanisms for retarding the increases in their plasma levels that would otherwise occur after protein ingestion, inasmuch as these compounds are metabolized only marginally in the liver. In contrast, dietary phenylalanine, tyrosine, and methionine are removed from the bloodstream both by insulin-mediated tissue uptake and hepatic metabolism. This difference probably explains the greater amplitude of the daily rhythms in plasma branched-chain amino acids and their greater percent decreases after glucose consumption. It may also have contributed to the large inter-individual variations that we observed in LNAA concentrations. (These variations could also be explained by the presence of volunteers of both sexes in

TABLE 1

| Glucose Dose (g) | Time after glucose ingestion (min) | Plasma Amino Acid Levels after Glucos Ingestion Plasma amino acid levels (nmoles/ml) | | | | | | | | |
|---|---|---|---|---|---|---|---|---|---|---|
| | | Val | Iso | Leu | Met | Tyr | Phe | Trp | LNAA | Trp/LNAA |
| 0 | 0 | 209 ± 15 | 59 ± 6 | 120 ± 11 | 24 ± 2 | 61 ± 3 | 54 ± 2 | 42 ± 4 | 528 ± 37 | .079 |
|  | 60 | 190 ± 13 | 52 ± 6 | 109 ± 9 | 23 ± 4 | 55 ± 2 | 49 ± 1 | 38 ± 4 | 478 ± 32 | .079 |
|  | 120 | 208 ± 13 | 52 ± 5 | 115 ± 9 | 24 ± 1 | 59 ± 5 | 53 ± 1 | 39 ± 3 | 512 ± 32 | .075 |
| 6 | 0 | 220 ± 19 | 60 ± 7 | 113 ± 11 | 24 ± 4 | 57 ± 8 | 50 ± 3 | 46 ± 4 | 522 ± 47 | .088 |
|  | 60 | 201 ± 15 | 51 ± 4 | 100 ± 12 | 21 ± 3 | 51 ± 7 | 46 ± 2 | 43 ± 4 | 47 ± 33 | .092 |
|  | 120 | 200 ± 16 | 51 ± 5 | 101 ± 9 | 22 ± 3 | 50 ± 6 | 47 ± 3 | 41 ± 4 | 471 ± 37 | .086 |
| 12.5 | 0 | 255 ± 47 | 65 ± 5 | 117 ± 10 | 27 ± 2 | 58 ± 4 | 54 ± 4 | 45 ± 2 | 574 ± 15 | .079 |
|  | 60 | 226 ± 48 | 53 ± 4 | 96 ± 10 | 25 ± 1 | 52 ± 3 | 50 ± 3 | 40 ± 1 | 501 ± 66 | .080 |
|  | 120 | 221 ± 98 | 48 ± 3 | 95 ± 9 | 23 ± 1 | 50 ± 3 | 46 ± 2 | 41 ± 1 | 582 ± 49 | .084 |
| 25 | 0 | 294 ± 50 | 71 ± 6 | 130 ± 13 | 26 ± 3 | 63 ± 3 | 56 ± 3 | 47 ± 2 | 639 ± 79 | .073 |
|  | 60 | 218 ± 29 | 48 ± 4 | 84 ± 10 | 21 ± 2 | 49 ± 2 | 47 ± 4 | 42 ± 2 | 466 ± 45 | .091 |
|  | 120 | 212 ± 26 | 46 ± 4 | 91 ± 8 | 19 ± 2 | 46 ± 2 | 41 ± 2 | 41 ± 3 | 454 ± 40 | .089 |
| 50 | 0 | 262 ± 40 | 61 ± 4 | 114 ± 11 | 26 ± 2 | 59 ± 4 | 50 ± 2 | 46 ± 2 | 573 ± 60 | .080 |
|  | 60 | 215 ± 32 | 48 ± 2 | 93 ± 11 | 21 ± 2 | 43 ± 3 | 50 ± 4 | 40 ± 1 | 469 ± 52 | .085 |
|  | 120 | 170 ± 30 | 36 ± 4 | 72 ± 10 | 18 ± 2 | 40 ± 4 | 37 ± 2 | 35 ± 2 | 372 ± 50 | .094 |

Sum of the LNAA: total concentration of leucine, isoleucine, valine, methionine, phenylalanine, and tyrosine; TRP/LNAA: ratio of tryptophan to the sum of the LNAA, measured 0, 60 and 120 min after 6 nonobese, fasting subjects ingested 0, 6, 12.5, 25 or 50 g of glucose. All plasma amino acids, except tryptophan, were measured on a Beckman amino acid analyzer. Tryptophan was measured by the method of Denckla and Dewey. Data are expressed as means ± S.E.M.

our study, females tending to have lower LNAA concentrations than males.

EXAMPLE II

Sprague-Dawley rats fasted overnight received glucose (3 g/kg) or a placebo by intubation (orally), and then, 30 minutes later, tyrosine (100 mg/kg, also by intubation). They were killed an hour after the tyrosine treatment. Serum tyrosine levels were approximately the same in the two groups i.e., 20.9 micrograms/ml in the tyrosine-alone group, and 19.4 in the tyrosine-plus-glucose animals. However, brain tyrosine levels were significantly different (23.1 vs 16.2) and the brain/serum tyrosine ratios also differed (1.50 vs 0.78).

A second set of Sprague-Dawley rats fasted overnight received the same tyrosine and glucose doses, but given concurrently. Ninety minutes later, the brain/serum tyrosine ratios were 0.77 vs 1.04 in the tyrosine-alone and tyrosine-plus-glucose groups and 0.74 in untreated control animals. The ratios of plasma tyrosine to plasma levels of its amino acid competitors were 0.397 vs 0.463 (which differ significantly), and 0.100 in untreated controls. After 180 minutes, this latter ratio was 0.265 vs 0.329 (and 0.124 in untreated controls).

EXAMPLE III

Sprague-Dawley rats (150 g) were fasted overnight and at 9:00 a.m. the following day were administered tyrosine alone, tyrosine and glucose or a placebo. The rats then were killed 90 minutes later and the brain and plasma levels of tyrosine were measured. The results are shown in Table 2.

TABLE 2

|  | Serum Tyrosine μg/ml | Brain Tyrosine μg/ml | Brain Serum | Serum Tyrosine Serum LNAA* |
|---|---|---|---|---|
| Control | 12.6 ± .6 | 12.1 ± 3.2 | 0.96 ± 0.2 | .145 |
| Tyrosine 100 mg/kg | 23.2 ± 2.1 | 23.0 ± 2.2 | 1.02 ± 0.1 | .304 |
| Tyrosine 100 mg/kg Glucose 1 g/kg | 25.2 ± 2.2 | 25.5 ± 1.4 | 1.01 ± 0.2 | .359 |
| Tyrosine 100 mg/kg Glucose 3 g/kg | 25.6 ± 2.8 | 35.0 ± 6.1 | 1.41 ± 0.2 | .454 |
| Tyrosine 100 mg/kg Glucose 6 g/kg | 15.7 ± 1.5 | 23.4 ± 0.9 | 1.55 ± 0.4 | .316 |

*LNAA equals sum of

When the tyrosine was given with 15X and 30X as much glucose (i.e., 1.5 g/kg or 3.0 g/kg), its effects on brain tyrosine and the tyrosine/LNAA ratios were much greater than when it was given alone; this is because, at these doses, serum tyrosine levels were still allowed to rise, but serum LNAA levels fell. When the tyrosine was accompanied by 60X as much glucose (6.0 g/kg), the effects on brain tyrosine and the serum tyrosine/LNAA ratio were not enhanced, because this amount of carbohydrate attenuated the effect of the tyrosine on blood tyrosine levels. Hence, it is important that the tyrosine and carbohydrate be administered in proper ratios.

I claim:

1. A composition which, when administered to an animal, effects an increase of brain tyrosine levels as compared to the administration of tyrosine alone, which consists essentially of an amount of tyrosine effective to increase brain tyrosine levels and a carbohydrate in an amount effective to cause insulin to be released in the animal.

2. The composition of claim 1 wherein the carbohydrate is sugar.

3. The composition of claim 2 wherein the sugar is sucrose.

4. The method of increasing brain tryosine levels in an animal, which comprises administering to the animal a composition consisting essentially of an amount of tyrosine effective to increase brain tyrosine levels and a carbohydrate in an amount effective to cause insulin to be released in the animal.

5. The method of claim 4 wherein the carbohydrate is a sugar.

6. The method of claim 4 wherein the sugar is sucrose.

7. The composition of claim 1 which includes caffeine.

8. The composition of claim 2 which includes caffeine.

9. The composition of claim 3 which includes caffeine.

10. The method of claim 4 wherein the composition includes caffeine.

11. The method of claim 5 wherein the composition includes caffeine.

12. The method of claim 6 wherein the composition includes caffeine.

* * * * *